US006855837B2

(12) United States Patent
Ekblom

(10) Patent No.: US 6,855,837 B2
(45) Date of Patent: Feb. 15, 2005

(54) PROCESS FOR THE PREPARATION OF STANOL ESTERS

(75) Inventor: Jari Ekblom, Rasio (FI)

(73) Assignee: Raisio Benecol, Ltd., Raisio (FI)

( * ) Notice: Subject to any disclaimer, the term of this patent is extended or adjusted under 35 U.S.C. 154(b) by 0 days.

(21) Appl. No.: 10/234,138

(22) Filed: Sep. 5, 2002

(65) Prior Publication Data

US 2003/0004361 A1 Jan. 2, 2003

Related U.S. Application Data

(63) Continuation of application No. 09/367,836, filed as application No. PCT/FI98/00166 on Feb. 25, 1998, now abandoned.

(30) Foreign Application Priority Data

Feb. 26, 1997 (FI) .................................................. 970802

(51) Int. Cl.$^7$ ................................................ C07J 9/00
(52) U.S. Cl. ...................................................... 552/544
(58) Field of Search ........................................ 552/544

(56) References Cited

U.S. PATENT DOCUMENTS

| 4,428,885 A | 1/1984 | Higaki et al. ................ 260/410 |
|---|---|---|
| 5,502,045 A | 3/1996 | Miettinen et al. ............ 514/182 |

FOREIGN PATENT DOCUMENTS

| EP | 0 911 385 A1 | 4/1999 |
|---|---|---|
| WO | 92/19640 | 11/1992 |
| WO | 98/01126 | 1/1998 |
| WO | 98/06405 | 2/1998 |
| ZA | 21 01 96/7616 | 5/1998 |

OTHER PUBLICATIONS

Sugano et al., "Lipid–Lowering Activity of Phytostanols in Rats." Atherosclerosis, vol. 24, pp. 301–309, 1976.*
Augustine et al., "The Palladium Catalyzed Hydrogenation of Cholesterol.", Organic Preparations and Procedures, vol. 1(2), pp. 107–109, 1969.*
Declaration by Ilkka Etupaltta, Jan. 18, 2001.
Serum Plant Sterols and Cholesterol Precursors Reflect Cholesterol Absorption and Synthesis in Volunteers of a Randomly Selected Male Population, Miettinen et al., Am. J. Epiderm., vol. 131, No. 1:20–31, 1990.
Fate of Dietary Sterols in Hydrogenated Oils and Fats, P.W. Parodi, J.Am. Oil Chem. Soc., vol. 52:345–348, 1975.
Saturated Sterols (Stanols) in Unhydrogenated and Hydrogenated Edible Vegetable Oils and in Cereal Lipids, Dutta et al., J. Sci. Food Agric., vol. 17:383–391, 1996.

Comparison of the effects of plant sterol ester and plant stanol ester–enriched margarines in lowering serum cholesterol concentrations in hypercholesterolaemic subjects on a low–fat diet, Eur. J. Clin. Nutrition, vol. 54, 715–725, 2000.
Effects of Low–Fat Yogurt with Plant Stanol Esters and of Consumption Frequency on LDL–Cholesterol Levels, J. Plat et al., Summary of Presentation at 92nd AOCS Annual Meeting and Expo, May 13–16, 2001, Minneapolis, Minnesota, USA.
Front page of WO 92/19640, Nov. 12, 1992.
PCT Applicant's Guide (Swedish Patent Office as ISA), Jul. 1999.
PCT Applicant's Guide (Sweidsh Patent Office as IPEA), Jul. 1998.
Efficacy of spreads enriched with stanol–stearate esters on blood cholesterol levels, Annex I filed with the Opponent's further submissions of Jun. 27, 2000.
Stanol Components in Edible Fats and Oils, M. Sugano et al., Sci. Byull. Fac. Agr. Kyushu Univ., vol. 32, No. 1:21–28, 1977.
Ullmann's Encyclopedia of Industrial Chemistry, vol. A16:152–153, 1990.
Elintarvike–tekniikan Perusteet, M.Hiros et al., VAP-K–kustannus, Helsinki, 1990, * translation of passage bridging pp. 240–241.
Hydrogenation of sterol esters. Demonstration of hydrogenation of sterol moiety, Annex II filed with the Opponent's further submission of Jun. 27, 2000.
Augustine et al., "The Palladium Catalyzed Hudrogenation of Cholesterol", Organic Preparations and Procedures 1(2), 107–109 (1969).
Sugano et al., "Lipid–Lowering Activity of Phytostanols in Rats", Atherosclerosis, 24 (1976) 301–309.

* cited by examiner

Primary Examiner—Barbara P. Badio
(74) Attorney, Agent, or Firm—Arent Fox PLLC

(57) ABSTRACT

The invention relates to a process for the preparation of stanol esters by hydrogenating a sterol blend in a hydrogenation solvent and at an elevated temperature in the presence of a hydrogenation catalyst, by removing the hydrogenation catalyst from the obtained hot reaction solution, by transesterifying the intermediate stanol blend with a fatty acid methyl ester at an elevated temperature and in the presence of a transesterification catalyst, and by finally purifying the stanol ester blend thus obtained. According to the invention, the intermediate stanol blend is neither crystallized nor removed from the reaction solution but the hydrogenation solvent is replaced therein at least in part by a transesterification reagent. Alternatively, the hydrogenation solvent may also be used as the transesterification solvent, and preferably also as the transesterification reagent.

29 Claims, No Drawings

PROCESS FOR THE PREPARATION OF STANOL ESTERS

This is a Continuation of Application Ser. No. 09/367,836 filed Nov. 22, 1999 now abandoned, which is a national stage entry of International Application No. PCT/FI98/00166, filed Feb. 25, 1998. The disclosure of the prior application(s) is hereby incorporated by reference herein in its entirety.

The present invention relates to a process for the preparation of stanol esters, and in particular to a process wherein stanol esters are prepared by hydrogenating at least one sterol in a solvent and at an elevated temperature in the presence of a hydrogenation catalyst to the corresponding stanol or stanol blend, by removing the hydrogenation catalyst from the obtained reaction solution, by transesterifying the stanol or the stanol blend with a lower alkyl ester at an elevated temperature and in the presence of a transesterification catalyst, and by finally purifying the stanol ester or stanol ester blend thus obtained.

Sterols are compounds commonly present in plants and animals, although in small concentrations. The sterol compound most commonly present in animals is cholesterol. The sterol material present in plants is usually composed of several sterol structures which resemble each other structurally. The most common of the latter are β-sitosterol, campesterol and stigmasterol. Depending on the plant species, there may also be present numerous other compounds resembling the above-mentioned sterols, for example brassicasterol in rape, α-sitosterol and betulinol in birch, methylene cycloartanol and cycloartenol, avenasterols, etc.

The sterols of wood material also include saturated sterol compounds wherein particularly the double bond between carbon atoms 5 and 6 of the sterol structure is hydrogenated to a saturated carbon-carbon bond. These compounds are called stanols. The stanol corresponding to the most common plant sterol, β-sitosterol, is thus β-sitostanol. Hydrogenation of sterols is described e.g. in Organic Preparations and Procedures 1 (2) (1969) 107–109 (Augustine, R. L. and Reardon Jr. E. J.: The Palladium catalyzed hydrogenation of cholesterol) and Atherosclerosis 24 (1975) 301–309 (Sugano, M. et al.: Lipid-lowering activity of phytosterols in rats).

Cholesterol is a compound indispensable for human subjects, as for other vertebrates, for example as an ingredient of cell structures. In high concentrations, however, cholesterol is detrimental, since it accumulates on the walls of blood vessels and thereby increases the risk of cardiovascular diseases.

It has been observed in investigations that plant sterol compounds, and in particular plant stanol compounds, added to the diet lower the blood serum cholesterol concentration in human subjects. When it is desired to use compounds derived from plant sterols for the lowering of cholesterol levels, it is important in terms of the efficacy and usability of the said compounds that they are in a suitable chemical and physical form.

U.S. Pat. No. 5,502,045 (Miettinen, T., et al.) suggests that the most advantageous form of use of plant sterol compounds is the intake of these compounds in the form saturated to stanols and esterified with fatty acids, in which case, on the one hand, the functional efficacy of the compounds is highest and, on the other hand, being fat-soluble they can easily be added to various foods.

The method conventionally used for preparing the compounds concerned, so-called stanol esters, is a procedure according to which the sterol is first hydrogenated catalytically in a hydrogenation solvent. The hydrogenated sterol (stanol) is crystallized and subsequently isolated by filtration from the reaction mixture, and is thereafter transferred to a transesterification process, in which the transesterification reagent is typically a vegetable oil methyl ester. (South African patent ZA 96/7616, Wester, I. et al.).

The preparation method described above, known per se, has the disadvantage that the price of the stanol ester produced by the method becomes relatively high owing to the high investment costs required by the filtration of the crystallized stanol intermediate. It has been thought that in order to obtain a sufficiently pure end product the stanol intermediate must be isolated from the reaction mixture before the transesterification process.

The object of the present invention is thus to provide a more advanced method than previously for the preparation of fat-soluble stanol esters, simplifying the preparation process of stanol esters and thereby lowering the investment costs of the plant for the preparation of stanol esters and, owing to the almost quantitative yield, at the same time maximizing the production of a stanol ester end product of a sufficiently high quality.

The present invention thus provides a stanol ester preparation method of the type mentioned in the preamble, the principal characteristics of the process being stated in the accompanying claims.

The invention is based on the idea that the investment costs of a plant for the preparation of stanol esters can be lowered substantially by omitting the crystallization of the stanol intermediate and the filtration of the crystalline stanol intermediate from the reaction mixture, when the hydrogenation solvent is left in the reaction solution from which the hydrogenation catalyst has been removed. When necessary, the hydrogenation solvent is removed from the reaction mixture only after adding the transesterification reagent and the transesterification solvent, if any, to the reaction mixture. Preferably, however, the hydrogenation solvent used is one which serves as the solvent and reagent also in the transesterification.

When the stanol formed as an intermediate in the hydrogenation reaction is not isolated from the reaction mixture before the transesterification step, there is achieved not only a lowering of the investment costs but also a nearly quantitative yield of the end product, since yield losses relating to the intermediate are avoided, which losses would otherwise be inevitable in the isolation and filtration of the crystalline intermediate.

In an especially preferred embodiment of the invention, a fatty acid methyl ester of vegetable oil origin is used as the transesterification reagent and possibly as the hydrogenation solvent. It is especially advantageous to use a hydrogenation solvent having a lower boiling point than the transesterification reagent, in which case the hydrogenation solvent can be removed by distillation from a reaction solution to which the transesterification reagent is added or has been added. In this manner, the passing of saturated fatty acids to the stanol ester end product is avoided. In this case the hydrogenation solvent used is preferably a methyl ester of coconut fatty acids or palm kernel oil fatty acids, whereas the transesterification reagent is a methyl ester of rapeseed oil fatty acids. The source of the fatty acid or fatty acid blend alcohol ester used as the transesterification reagent may be the fatty acids of any fat, oil, or blends thereof.

Stanol esters can indeed be prepared according to the invention, without the crystallization and isolation of stanols, also by using conventional hydrogenation solvents instead of fatty acid methyl esters. In this case the suitable solvents include alcohols, hydrocarbons and ethers, such as tetrahydrofuran. It is particularly advantageous to use a high boiling aromate-free and thus inert aliphatic hydrocarbon as the hydrogenation solvent, since it does not react with the transesterification reagent in the transesterification step. This alternative is preferable when it is desired to prevent the incorporation of saturated fatty acids into the stanol ester product. In this case, the fatty acid methyl ester used in the transesterification is added to the post-hydrogenation reaction mixture from which the hydrogenation catalyst has been removed, and thereafter the hydrogenation solvent is removed by distillation before the actual transesterification. The use of fatty acid methyl esters can, however, be justified, since they have a higher flash point than have conventional solvents, such as n-propanol, which means improved fire safety.

The hydrogenation catalyst used is preferably a noble metal catalyst, such as palladium on carbon or on an organic polymer compound. The hydrogenation is preferably carried out at a temperature of at most about 120° C., but the hydrogen pressure may vary in a wide range. Also the amount of the hydrogenation catalyst used in the reaction may vary, but may preferably be used in an amount of 0.1–2% active ingredient of the weight of the sterol to be hydrogenated. By this selection of hydrogenation conditions, the hydrogenation can be carried out at a high concentration of solids, rapidly, and without the formation of detrimental degradation products.

At the end of the hydrogenation reaction, the hydrogenation catalyst is removed by filtration from the hot reaction mixture. The filtration of the hydrogenation catalyst is problem-free and does not require high investments.

The transesterification catalyst used is preferably an alkali metal alcoholate, such as sodium methylate or sodium ethylate. In this case the amount of transesterification catalyst is preferably 0.1–1% of the weight of the reaction solution.

The transesterification is preferably carried out at 100–130° C. and by using a stoichiometric excess of the transesterification reagent, for example a double excess, relative to the stanol or the stanol blend.

In the process according to the invention, the starting substance used may be any sterol or sterol blend obtainable from plants, and in principle also animal sterols, for example cholesterol or lanosterol. Preferably, however, a sterol blend is hydrogenated which contains mainly sitosterol and additionally campesterol and possibly stigmasterol. Especially preferably, a sterol blend based on tall oil or vegetable oil is hydrogenated.

It has now been shown, surprisingly, that even if the crystallization of the stanol intermediate and the removal of the crystals by filtration, regarded as indispensable in the prior known method for the preparation of stanol esters, are omitted, the stanol ester end product can, however, be recovered in a sufficiently pure state and, above all, with a higher yield, by using after the transesterification step purification processes known per se. Even if the concentration of impurities (e.g. dehydrogenation products of tocopherols and sterols, long-chained hydrocarbons, and fatty alcohols) formed in the reaction and brought in by the raw materials were rather high, their removal by the method according to the invention is possible by using, for example, steam distillation and adsorption, known per se. In addition to these purification procedures, for example, thin film evaporation can also be used.

DETAILED DESCRIPTION OF THE INVENTION

In the first step of the reaction series, the hydrogenation, it is preferable to use as catalyst a noble metal catalyst such as palladium, platinum or ruthenium. Also possible is, for example, Raney nickel, cobalt, or copper chromite compounds. The catalyst support may be, for example, carbon, alumina, silica gel, or an organic polymeric compound.

The hydrogenation is most preferably carried out at a temperature below about 120° C. The pressure in the reaction mixture may vary widely. The catalyst concentration may also vary within a wide range. By keeping the temperature about the above mentioned level the formation of by-products (e.g. splitting off reactions of hydroxyl) is most effectively avoided.

By an appropriate selection of the hydrogenation conditions, a situation is thus arrived at wherein the hydrogenation can be carried out at a high solids concentration, rapidly, and without the formation of detrimental degradation products.

When the hydrogenation reaction has been brought to completion, the hydrogenation catalyst is removed from the hot reaction mixture by filtration.

If the removal of a portion of the hydrogenation solvent (methyl ester or some other solvent) is desired before the transesterification, it must be done in the subsequent step. This is done by adding the fatty acid methyl ester to be used in the transesterification to the hydrogenation reaction mixture before the distillation or simultaneously with the distillation. The conditions used in the distillation of the solvent are, of course, dependent on the physical properties of the solvent used. It is, however, a marginal condition that the boiling point of the hydrogenation solvent must deviate sufficiently (must be lower) from the boiling point of the fatty acid ester serving as the reagent, in order for fractional removal of the hydrogenation solvent to be possible.

The next step in the preparation of stanol ester is the transesterification of the stanol with the fatty acid ester contained in the reaction solution.

The esterification reaction per se may take place under the effect of any reagent catalyzing transesterification (examples include inorganic acids, toluene sulfonic acids, organostannates or alkaline catalysts). However, it is especially preferable to use in the transesterification alkali metal alcoholates, for example, sodium methylate or sodium ethylate, transesterification catalysts well known per se from the literature in the field. The catalyst concentration and the other reaction conditions required vary largely as a function of the type of catalyst used. In a reaction occurring under the effect of sodium methylate it is preferable to use the catalyst in an amount of approx. 0.1–1% of the amount of the reaction mixture. The temperature being approx. 100–130° C., the reaction occurs completely within approx. 60–180 min when an approx. double stoichiometric excess of the fatty acid methyl ester relative to the stanol amount is used in the transesterification.

After the reaction step, the impurities formed in the reaction and brought in with the raw material (catalysts, sterol degradation products, etc.) can be removed by means of water washes and by water vapor distillation and additionally, when necessary, by causing the impurities to be absorbed into a suitable absorbent material (examples include activated carbon and/or bleaching earth). Steam distillation is a necessary purification step also for the removal of any reagent excess. Suitable conditions in the steam distillation step, when the reagent is the methyl ester of rapeseed fatty acids, are: temperature 180–230° C., pressure 1–10 mbar, and the amount of steam to be fed approx. 2–10% of the total amount of the reaction mixture.

Examples on the preparation of stanol esters according to the invention are presented below.

EXAMPLE 1

300 g of a sterol derived from tall oil (10% campesterol/stanol, 90% β-sitosterol/stanol) was slurried into 700 g of coconut fatty acid methyl ester (which contains primarily $C_6$–$C_{14}$ fatty acid esters). A Pd catalyst bound to polypropylene fiber, Smop-20 (manufacturer Smoptech, Turku, Finland), was added in an amount of 0.7% of the amount of sterol, the temperature was raised to 120° C., and the reaction autoclave was rinsed with nitrogen. Thereafter hydrogen was directed to the reaction mixture for 130 min. During the hydrogenation the pressure of the reaction mixture varied within a range of 1–2 atm. The hydrogenation catalyst was removed by distillation from the hot reaction mixture. Thereafter 360 g of rapeseed oil fatty acid methyl ester was directed to the reaction mixture, and the coconut methyl ester which had served as a solvent was removed by distillation at a temperature of 140° C. and a pressure of 8 mbar. Thereafter 3 g of sodium methylate was added as an esterification catalyst, and the esterification reaction was allowed to occur at 120° C. for 1.5 h at a pressure of 5 mbar. The ester product was washed twice with water, and the excess methyl ester reagent and impurities were steam distilled at a temperature of 200° C. and a pressure of 3 mbar. The product was filtered while hot through bleaching earth and a layer of activated carbon. The stanol ester product contained free fatty acids 0.02%, fatty acid methyl esters 0.3%, and unesterified sterol-derived compounds 0.8%. The melting point of the stanol ester was 36–39° C. according to DSC determination.

EXAMPLE 2

295 g of a sterol derived from vegetable oil (25% campesterol, 55% β-sitosterol and 15% stigmasterol) was slurried into 705 g of coconut fatty acid methyl ester (which contains primarily $C_6$–$C_{14}$ fatty acid esters). A Pd/C catalyst was added (5% Pd on a carbon support, 0.2% palladium of the amount of sterol), the temperature was raised to 120° C., and the reaction autoclave was rinsed with nitrogen. After the nitrogen had first been replaced by a hydrogen atmosphere, hydrogen was directed to the reaction mixture for 110 min. During the hydrogenation the pressure of the reaction mixture was 1–2 atm.

The hydrogenation catalyst was removed from the hot reaction mixture by filtration.

Thereafter 3 g of sodium methylate was added as the esterification catalyst, and the esterification reaction was allowed to occur at a temperature of 125° C. for 1.5 h at a pressure of 5 mbar, whereby the formed methanol was at the same time removed. The ester product was washed twice with water, and the excess methyl ester reagent and impurities were steam distilled first at a temperature of 140–145° C. and a pressure of 7–9 mbar. Finally the temperature was raised to 200–205° C. (pressure 3–4 mbar) in order to remove the higher boiling impurities. The product was filtered while hot through bleaching earth and a layer of activated carbon. The stanol ester product contained free fatty acids 0.025%, fatty acid methyl esters 0.3%, and unesterified sterol-derived products 0.6%. The melting point of the stanol ester was 93–97° C. according to DSC determination.

EXAMPLE 3

In a process according to Example 2, rapeseed oil methyl ester was used as the hydrogenation solvent and at the same time as the esterification reagent instead of coconut fat methyl ester. The reaction and the purification steps were carried out as in Example 2 (however, the temperature and pressure were 200–205° C./3–4 mbar throughout the steam distillation). The product obtained was a wax having a melting range of 98–104° C.

EXAMPLE 4

In this example, the hydrogenation solvent used was coconut fatty acid methyl ester, which was partly removed by distillation and replaced with rapeseed oil methyl ester before the transesterification.

250 g of a sterol derived from vegetable oil was slurried into 650 g of coconut fatty acid methyl ester. A Pd/C catalyst was added in an amount of 0.2%, and the sterol was hydrogenated as in the preceding examples.

The hydrogenation catalyst was removed from the hot reaction mixture by filtration.

Thereafter, 300 g of rapeseed oil methyl ester was added to the reaction mixture, and 300 g of the saturated coconut fatty acid ester was distilled at a temperature of 140–150° C. and a pressure of 7–9 mbar. The mixture was transesterified and purified in the manner described in the preceding examples. The reaction product was a light yellow wax having a melting range of 69–74° C.

EXAMPLE 5

In the process according to Example 1, a high boiling (distillation range 180–210° C.) aliphatic hydrocarbon free of aromatic compounds was used as the hydrogenation solvent instead of coconut fatty acid ester. The reactions and purification processes were carried out substantially in the manner described in Example 1. The reaction product obtained was a wax corresponding to the product of Example of 1 and having a melting range of 37–40° C.

What is claimed is:

1. A process for preparing a stanol fatty acid ester or mixture thereof, the process comprising:

hydrogenating a sterol or mixture thereof in a hydrogenation solvent in the presence of a hydrogenation catalyst at elevated temperatures, to produce a stanol or mixture thereof;

thereafter separating the hydrogenation catalyst and the stanol or mixture thereof without separating the stanol or mixture thereof and the hydrogenation solvent;

thereafter combining the stanol or mixture thereof and the hydrogenation solvent with (1) a transesterification reagent comprising a lower alkyl fatty acid ester and (2) a transesterification catalyst;

optionally, simultaneous with or after the combining of the stanol or mixture thereof with the transesterification reagent, separating at least a portion of the hydrogenation solvent and the stanol or mixture thereof; and transesterifying the stanol or mixture thereof with the lower alkyl fatty acid ester, to produce a stanol fatty acid ester or mixture thereof.

2. The method of claim 1, wherein the optional separating step is performed.

3. The method of claim 2, wherein the optional separating step is performed simultaneous with the combining of the stanol or mixture thereof with the transesterification reagent.

4. The method of claim 2, wherein the optional separating step is performed after the combining of the stanol or mixture thereof with the transesterification reagent.

5. The method of claim 1, wherein the transesterification reagent comprises a lower alkyl fatty acid ester of vegetable oil origin.

6. The method of claim 5, wherein the lower alkyl fatty acid ester comprises a methyl fatty acid ester.

7. The method of claim 6, wherein the methyl fatty acid ester is rapeseed oil methyl fatty acid ester.

8. The method of claim 1, wherein the hydrogenation solvent comprises a lower alkyl fatty acid ester.

9. The method of claim 8, wherein the hydrogenation solvent comprises a lower alkyl fatty acid ester of vegetable oil origin.

10. The method of claim 9, wherein the lower alkyl fatty acid ester comprises a methyl fatty acid ester.

11. The method of claim 10, wherein the methyl fatty acid ester is coconut methyl fatty acid ester.

12. The method of claim 1, wherein the hydrogenation solvent comprises an inert aliphatic hydrocarbon or an alcohol.

13. The method of claim 1, wherein the hydrogenation catalyst comprises a noble metal.

14. The method of claim 1, wherein the transesterification catalyst comprises an alkali metal alcoholate.

15. The method of claim 1, wherein the transesterifying step is performed at a temperature of 100–130° C. and the transesterification catalyst is present in stoichiometric excess relative to the stanol or mixture thereof.

16. The method of claim 1, wherein the sterol or mixture thereof is from tall oil or vegetable oil.

17. The method of claim 1, wherein the sterol or mixture thereof comprises sitosterol.

18. The method of claim 1, wherein the hydrogenating step is performed at a temperature of below 120° C.

19. The method of claim 2, wherein the hydrogenation solvent has a boiling point which is lower than the boiling point of the transesterification reagent, and the optional separating step comprises fractionally distilling the hydrogenation solvent.

20. A process for preparing a stand fatty acid ester or mixture thereof, the process comprising:

hydrogenating a sterol or mixture thereof in a solvent comprising a lower alkyl fatty acid ester, in the presence of a hydrogenation catalyst at elevated temperatures, to produce a stanol or mixture thereof;

thereafter separating the hydrogenation catalyst and the stanol or mixture thereof without separating the stanol or mixture thereof and the solvent;

thereafter combining the stanol or mixture thereof and the solvent with a transesterification catalyst;

transesterifying the stanol or mixture thereof with the lower alkyl fatty acid ester, to produce a stanol fatty acid ester or mixture thereof.

21. The method of claim 20, wherein the solvent comprises a lower alkyl fatty acid ester of vegetable oil origin.

22. The method of claim 21, wherein the lower alkyl fatty acid ester comprises a methyl fatty acid ester.

23. The method of claim 20, wherein the hydrogenation catalyst comprises a noble metal.

24. The method of claim 20, wherein the transesterification catalyst comprises an alkali metal alcoholate.

25. The method of claim 20, wherein the transesterifying step is performed at a temperature of 100–130° C. and the transesterification catalyst is present in stoichiometric excess relative to the stanol or mixture thereof.

26. The method of claim 20, wherein the sterol or mixture thereof is from tall oil or vegetable oil.

27. The method of claim 20, wherein the sterol or mixture thereof comprises sitosterol.

28. The method of claim 1, wherein the hydrogenating step is performed at a temperature of below 120° C.

29. A process for preparing a stanol fatty acid ester or mixture thereof, the process comprising:

hydrogenating a sterol or mixture thereof in a hydrogenation solvent in the presence of a hydrogenation catalyst at elevated temperatures, to produce a stanol or mixture thereof;

thereafter separating the hydrogenation catalyst and the stanol or mixture thereof without separating the stanol or mixture thereof and the hydrogenation solvent;

thereafter combining the stanol or mixture thereof and the hydrogenation solvent with (1) a transesterification reagent comprising a lower alkyl fatty acid ester and (2) a transesterification catalyst;

optionally, simultaneous with or after the combining of the stand or mixture thereof with the transesterification reagent, separating at least a portion of the hydrogenation solvent and the stanol or mixture thereof; and transesterifying the stanol or mixture thereof with the lower alkyl fatty acid ester, to produce a stanol fatty acid ester or mixture thereof in an transesterification reaction, wherein said transesterification reaction occurs completely within 180 minutes.

* * * * *